(12) United States Patent
Huotilainen et al.

(10) Patent No.: US 10,388,011 B2
(45) Date of Patent: Aug. 20, 2019

(54) REAL-TIME, FULL WEB IMAGE PROCESSING METHOD AND SYSTEM FOR WEB MANUFACTURING SUPERVISION

(71) Applicant: ABB Schweiz AG, Baden (CH)

(72) Inventors: Tommi Huotilainen, Helsinki (FI); Seppo Riikonen, Espoo (FI); Myron Laster, Acworth, GA (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 16/302,545

(22) PCT Filed: May 17, 2017

(86) PCT No.: PCT/EP2017/025138
§ 371 (c)(1),
(2) Date: Nov. 16, 2018

(87) PCT Pub. No.: WO2017/198348
PCT Pub. Date: Nov. 23, 2017

(65) Prior Publication Data
US 2019/0164276 A1    May 30, 2019

Related U.S. Application Data

(60) Provisional application No. 62/337,625, filed on May 17, 2016.

(30) Foreign Application Priority Data

Jul. 20, 2016 (EP) ..................................... 16180281

(51) Int. Cl.
*G06T 7/00* (2017.01)
*G01N 21/89* (2006.01)

(52) U.S. Cl.
CPC ........... *G06T 7/0004* (2013.01); *G01N 21/89* (2013.01); *G06T 2207/30124* (2013.01); *G06T 2207/30144* (2013.01)

(58) Field of Classification Search
CPC ... G01N 21/89; G01N 21/8901; G01N 21/896
(Continued)

(56) References Cited

U.S. PATENT DOCUMENTS 6,198,537 B1* 3/2001 Bokelman ............... G01N 21/89
131/905
6,950,547 B2* 9/2005 Floeder .................. G01N 21/89
382/141

(Continued)

FOREIGN PATENT DOCUMENTS

WO    2013182313 A1    12/2013

OTHER PUBLICATIONS

European Search Report Application No. 16180281.4 Completed: Jan. 31, 2017; dated Feb. 6, 2017 9 pages.
(Continued)

*Primary Examiner* — Yosef Kassa
(74) *Attorney, Agent, or Firm* — Whitmyer IP Group LLC

(57) ABSTRACT

A method for detection of distinctive features in a web being transported in a moving direction during a web manufacturing process including the steps of: a) acquiring an image of the web, including a plurality of pixels P i with i∈{1; . . . ; p}, b) identifying a plurality of regions of interest each corresponding to a distinctive feature by processing the plurality of pixels P i by: c) selecting a local pixel unit including a subset P j with j∈S ⊂ {1; . . . ; p} of the plurality of pixels, the subset i) being representative of a subregion of the digital image, and ii) different from previously selected local pixel units, d) deciding whether the local pixel unit is
(Continued)

of interest or not, i) if the local pixel unit is of interest, 1) identifying whether the local pixel unit is located within an impact area A k of a previously identified region of interest R k with k∈A⊆{1; . . . ; n}, 2) if the local pixel unit is not located within any impact area A k of any previously identified region of interest R k with k∈A⊆{1; . . . ; n}, or no regions of interest have previously been identified, (a) identifying the local pixel unit as a new region R n+1 of interest; (b) initializing an impact area A n+1 for the new region R n+1 of interest; (c) incrementing a counter n representative of the number of previously identified regions of interest; if the local pixel unit is located within an impact area A k 0 of a previously identified region of interest R k 0, (a) merging, depending on a merging condition, the local pixel unit with the previously identified region of interest R k 0, (b) if the merging condition is fulfilled, updating the impact area A k 0 of the region of interest R k 0; ii) preferably, if the local pixel unit is not of interest, identifying whether the local pixel unit is located within an impact area A k of a previously identified region of interest R k with k∈{1; . . . ; n},if the local pixel unit is located within an impact area A k 0 of a previously identified region of interest R k 0, updating the impact area A k 0; e) repeating steps b) through d) until at least essentially all pixels of the image have been processed.

19 Claims, 9 Drawing Sheets

(58) Field of Classification Search
USPC ....... 382/141, 149, 152, 170, 171, 209, 275, 382/282; 348/86, 88, 92, 100, 125
See application file for complete search history.

(56) References Cited

U.S. PATENT DOCUMENTS

| | | | | |
|---|---|---|---|---|
| 7,099,510 | B2* | 8/2006 | Jones | G06K 9/00248 348/142 |
| 7,375,806 | B2* | 5/2008 | Daul | G01N 21/86 356/236 |
| 7,382,457 | B2* | 6/2008 | Kiraly | G01N 21/8903 356/429 |
| 7,545,985 | B2* | 6/2009 | Zhang | G06K 9/036 382/224 |
| 9,031,312 | B2* | 5/2015 | Ribnick | G01N 21/89 382/141 |
| 2002/0110269 | A1 | 8/2002 | Floeder et al. | |
| 2004/0201669 | A1 | 10/2004 | Guha et al. | |

OTHER PUBLICATIONS

International Preliminary Report on Patentability Application No. PCT/EP2017/025138 Completed: Aug. 1, 2018; dated Aug. 1, 2018 15 pages.
International Search Report and Written Opinion of the International Searching Authority Application No. PCT/EP2017/025138 Completed: Jun. 29, 2017; dated Jun. 13, 2017 17 pages.
Lorita Angeline et al: "Multiple Vehicles License Plate Tracking and Recognition via Isotropic Dilation", Computational Intelligence, Communication Systems and Networks (CICSYN), 2011 Third International Conference on, Jul. 26, 2011, pp. 54-59.
Tappi Organization, "Equivalent Black Area (EBA) and Count of Visible Dirt in Pulp, Paper, and Paperboard by Image Analysis", T 563 pm-97, Published: Jan. 1, 2015, 8 pages.
Written Opinion of the International Preliminary Examining Authority Application No. PCT/EP2017/025138 dated May 18, 2018 5 pages.

* cited by examiner

REAL-TIME, FULL WEB IMAGE PROCESSING METHOD AND SYSTEM FOR WEB MANUFACTURING SUPERVISION

TECHNICAL FIELD

The invention pertains to the field of web manufacturing. In particular, it relates to a system and a method for full web real-time web based on inspection image processing in accordance with the preamble of the independent patent claim.

BACKGROUND

Web manufacturing refers to production and/or processing of long, thin sheets of bendable, flexible and/or soft material, in particular paper, cardboard, textile, plastic film, foil, (sheet) metal, and sometimes wire, commonly referred to as web. During production or processing, a web is generally transported over rollers in a moving direction. Between processing stages, webs may be stored and transported as rolls also referred to as coils, packages and doffs. A final result of web manufacturing usually comprises sheets being separated from the web by cutting or otherwise separating in a cross direction perpendicular to the moving direction. A main reason for work with webs instead of sheets is economics. Webs, being continuous, may generally be produced and/or processed at higher speeds than sheets, without start-stop issues which are inherent to production and/or processing of sheets.

For supervision and/or quality control of web manufacturing, web inspection systems, as described e.g. in US 2002/0110269 A1, are frequently applied which use digital imaging techniques, in particular image capture and image processing, for detecting defects or other anomalies. For web manufacturing of paper or cardboard, holes, spots and dirt particles are examples of strong defects, frequently briefly referred to as defects, whereas wrinkles, streaks and slime spots are examples of weak defects. Correspondingly, for web manufacturing of sheet metal makers, slag inclusions, cracks and scratches are examples of strong defects whereas weak cracks, weak scratches and indentations are examples of weak defects.

Defects give rise to local deviations of various characteristic image quantities, in particular of a pixel intensity level, from average and/or expected values. In the above examples, weak defects cause only a slight change in an intensity level of the digital video signal as compared to a mean variation of the intensity level measured from a faultless product. Strong defects, on the other hand, give generally rise to substantial deviations.

In paper and pulp making, dirt particles can reduce the quality of the product significantly. Currently available web inspections systems (WIS) for defect detection can possibly count less than 500 dirt particles per second per system and classify them based on their sizes. In such a situation, current systems are not capable of doing anything else for example detecting other kinds of defects.

A performance of currently available web inspection systems is not high enough to allow for classifying dirt particles online, i.e. in real-time, while simultaneously supporting full web measurement. Current solutions for the pulp and paper dirt analysis are based on snapshot images, limited cross direction (CD) band or scanning imaging methods; or they are not supporting really high dirt densities, i.e. dirt densities of over 1000, let alone over 10000 dirt particles per second, and thus are not capable of supporting full web coverage and very high density dirt analysis in real time.

One of the most beneficial supervision and/or quality control procedures is dirt counting and dirt area classification, which analyzes the content of foreign materials in the web. Several international standards have been published for the dirt analysis procedure, but most of them represent offline laboratory measurements and produce test reports of only a small portion of the area of the manufactured pulp, paper, or paperboard product. ISO 5350 standard consists of four parts, under the general title "Pulps—Estimation of dirt and shives". The first two parts include transmission light based test procedures for laboratory sheets and mill sheeted pulp. Parts 3 and 4 are based on reflection measurement and Equivalent Black Area (EBA) method. Part 3 presents the visual inspection and Part 4 the instrumental inspection test methods. Also Tappi organization has published several Dirt analysis standards. Tappi T213 om-01 "Dirt in pulp—chart method" provides a test method for estimating the amount of dirt in pulp based on equivalent black area (EBA). In T213 a dirt speck is defined as the area of a round black spot on a white background of the TAPPI Dirt Estimation Chart. Tappi T 563 "Equivalent Black Area (EBA) and Count of Visible Dirt in Pulp, Paper, and Paperboard by Image Analysis" presents a method that uses image analysis to determine the level of dirt in pulp, paper, and paperboard based on EBA of dirt specks within the physical area range of 0.02 to 3.0 $mm^2$ reported in parts per million and the number of dirt specks per square meter.

Another quality factor in papermaking, but also for some other web products like for example pulp or glass fiber, is formation. Certain kinds of formation irregularities, e.g. non-uniform fiber clusters, are causing so-called flocs (which appear as cloudiness when looking through the product). Also in some web manufacturing products, formation irregularities are present in the form of uneven surfaces like for example coated paper with mottling, which can lead to unwanted, uneven print density and color variations. Earlier solutions for the paper or surface formation floc analysis were based on snapshot images, narrow band or scanning imaging methods and thus not capable of covering the whole web in real-time.

A performance of currently available web inspection systems is not sufficient for allowing for online, i.e. real-time, floc analysis including calculation of floc size distribution, while supporting full web measurement, i.e. analysis over the whole cross direction of the web.

SUMMARY

It is thus an objective of the invention to provide a method for on-line analysis of defects and/or formation irregularities in a web which overcomes the disadvantages as discussed above.

It is another objective of the invention to allow for simultaneous detection and analysis of defects of different types, in particular simultaneous detection of strong and weak defects, and/or simultaneous detection of defects and formation irregularities.

This objective is achieved by a method for detection and/or analysis of distinctive features, in particular defects and/or formation irregularities, in a web being transported in a moving direction during a web manufacturing process, the method comprising the steps of a) acquiring an image of the web, said image being representable as a digital image comprising a plurality of pixels $P_i$ with $i \in \{1; \ldots; p\}$, b) identifying a plurality of regions of interest each corresponding to a defect by processing the plurality of pixels $P_i$ by:
c) selecting a local pixel unit comprising a subset $P_j$ with $j \in S \subset \{1; \ldots; p\}$ of the plurality of pixels, said subset
   i. being representative of a subregion of the digital image, and
   ii. different from previously selected local pixel units,
d) deciding whether the local pixel unit is of interest or not,
   i. if the local pixel unit is of interest,
      1. identifying whether the local pixel unit is located within an impact area $A_k$ of a previously identified region of interest $R_k$ with $k \in A \subseteq \{1; \ldots; n\}$,
      2. if the local pixel unit is not located within any impact area $A_k$ of any previously identified region of interest $R_k$ with $k \in A \subseteq \{1; \ldots; n\}$, or no regions of interest have previously been identified,
         a. identifying the local pixel unit as a new region $R_{n+1}$ of interest;
         b. initializing an impact area $A_{n+1}$ for said new region $R_{n+1}$ of interest
         c. incrementing a counter n representative of the number of previously identified regions of interest;
      3. if the local pixel unit is located within an impact area $A_{k0}$ of a previously identified region of interest $R_{k0}$,
         a. merging, depending on a merging condition, the local pixel unit with said previously identified region of interest $R_{k0}$,
         b. if the merging condition is fulfilled, updating the impact area $A_{k0}$ of said region of interest $R_{k0}$;
   ii) preferably, if the local pixel unit is not of interest,
      1. identifying whether the local pixel unit is located within an impact area $A_k$ of a previously identified region of interest $R_k$ with $k \in \{1; \ldots; n\}$,
      2. if the local pixel unit is located within an impact area $A_{k0}$ of a previously identified region of interest $R_{k0}$, updating said impact area $A_{k0}$,
e) repeating steps b) through d) until at least essentially all pixels of the image have been processed.

The method allows for real time and online dirt count with 100% full web coverage including combined dirt count, defect imaging, advanced classification, and is capable of providing highly consistent, standardized detection results independent of an operator. Size classification conforming to industry standards or manually defined limits is available. Excellent laboratory correlations have been observed in experimental testing.

These and other aspects of the invention will become apparent from and elucidated with reference to the embodiments described hereinafter.

BRIEF DESCRIPTION OF THE DRAWINGS

The subject matter of the invention will be explained in more detail in the following text with reference to exemplary embodiments which are illustrated in the attached drawings, of which.

In principle, identical reference symbols in the figures denote identical parts. For better readability, certain reference symbols have been omitted in certain drawings or where identical parts occur repeatedly in a single drawing.

DETAILED DESCRIPTION

Figure 1A:
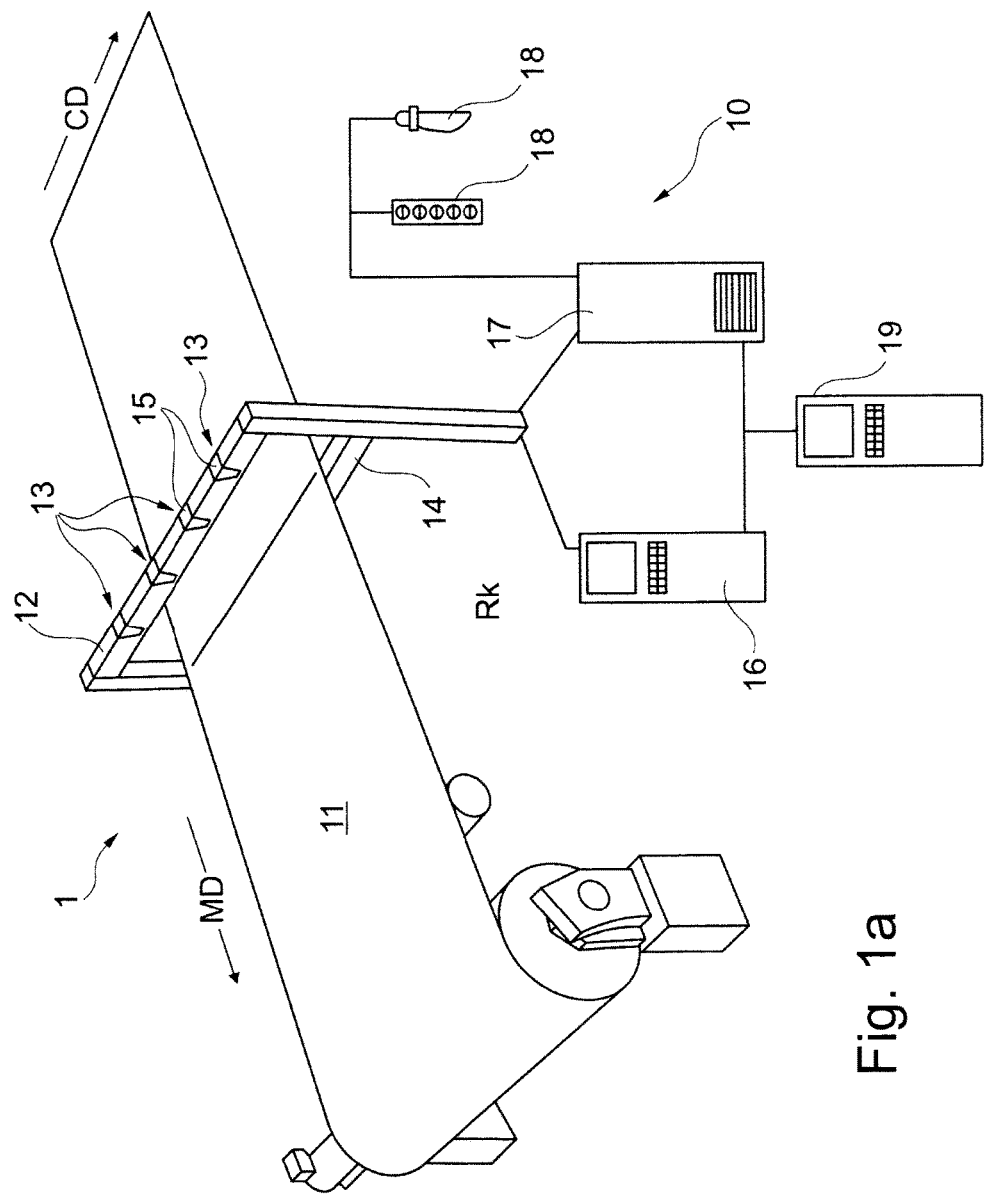
FIG. 1a illustrates a web inspection system which may be used for applying the method in accordance with the present invention to a web manufacturing process.

FIG. 1a illustrates a web inspection system which may be used for applying the method in accordance with the invention to a web manufacturing process.

During said web manufacturing process, a web 11 moves in a moving direction MD (briefly referred to as MD in what follows) underneath a line scan camera 12 which comprises a plurality of X pixel sensors 13 (of which only four are shown for clarity) arranged in a row extending in a cross CD direction of the web perpendicular to the moving direction (briefly referred to as CD in what follows). In operation, the line scan camera 12 scans the web as it passes by in order to acquire an image of said web and delivers a stream of line scans. A number Y of consecutive line scans may be combined into a two-dimensional digital image of a section of the web in moving direction, said digital image having a pixel dimension of X·Y pixels and comprising a plurality $P = X \cdot Y$ pixels $P_i$, with $i \in \{1; \ldots; X \cdot Y\}$, each pixel having one or more pixel values representative of a local color or total intensity, hue, saturation. The pixel values may have a certain bit depth or bit resolution, and may in particular be binary values representable by a single bit, which bit depth may correspond to a bit depth of the line scan camera, or have been obtained through up- or downsampling of the bit depth. For a line scan rate $f_{line}$, and a transport velocity $v_{MD}$ of the web in moving direction, a length of the section of the web in moving direction imaged this way is $Y \cdot v_{MD}/f_{line}$.

Typical line scan cameras include 512, 1024, 2048, 4096, 8192, 12288, 16384 or more pixels per line and some models include multiple lines, for example 2 or 4 lines, forming a kind of an area scan camera. Alternatively, one or more area scan cameras, which are based on different sensor dimensions, may be employed. Sometimes line scan and area scan cameras include special partial readout modes, which can be used in some cases to increase high speed line rates even more. Typical dynamic ranges of the cameras are 8, 10 or 12 bits. Streaming video input can include one or more sets or groups of pixels in CD and MD. For example a line scan camera with 8192 pixel sensor can send 8 CD direction pixels simultaneously.

While a digital image of the web thus acquired may be stored, in particular in a memory of a computer, in particular an standard computer, or a graphics processing unit, and the method in accordance with the invention be carried out on the stored digital image, in particular by an image processing program or application being executed on or by the computer, this is preferably not being done for various reasons related to efficiency.

Preferably, the method in accordance with the present invention is carried out on image data being streamed from the line scan or area scan camera, preferably in a single-pass algorithm, wherein each pixel or each group of pixels is processed only once (in contrast, e.g. to two-pass connected component algorithms, which generate a label image in a first pass, and updates/replaces labels in a second pass). In other words, once a particular pixel or pixel group has been processed, there is no possibility of going or referring back to that particular pixel or pixel group. A data window for the pixel or pixel group processing may be chosen depending on available real-time processing resources, for example an amount of high speed memory for intermediate processing results storage.

In the method in accordance with the present invention, regions of interest are identified in the two-dimensional digital image, with each region of interest found being deemed to correspond to a defect of the web, which may also be a formation irregularity, by processing the plurality of pixels $P_i$. In order to identify the regions of interest, processing is done repeatedly on subsets, preferably disjunct subsets (i.e. subsets having no pixel in common) of the digital image, or possibly of a scaled-up or scaled down-version of the digital image, referred to as local pixel units. In case of scanning with a line scan camera as described above, the local pixel units preferably have a dimension of x·y, wherein x≥1, with x<X and preferably x<<X, in particular with 2<x<8, e.g. x=4 in an x-direction corresponding to CD, and wherein y≥1, with y≤Y and preferably y<<Y, in particular with 2<y<4, in a y-direction corresponding to MD. A local pixel unit may thus correspond to a single pixel, or, in general, to a group of pixels or pixel group of the digital image. In particular, for multiple scan (for example 2 or 4 lines) line scan cameras, the local pixel unit can be for example 4·2, 8·2, 10·2, 8·4, or some other depending on also the region of interest detection requirements.

Each region of interest may thus be considered to represent a or correspond to a subset of pixels $P_r$, with $r \in R_k \subset \{1; \ldots; P\}$ of the plurality of pixels comprised by the digital image. Additionally or alternatively, each region of interest may be considered to represent a or correspond to a subset of all local pixel units that have been processed, as will become clear from the description to follow.

In a next step, it is decided, based on a decision rule, whether the local pixel unit is of interest or not. This is preferably done by means of thresholding, i.e. by checking whether an average, median, minimum or maximum of at least one of the pixel values of pixels of the local pixel unit is above or below a given or adaptive threshold. Various other rules may be defined for deciding whether the local pixel unit is of interest or not, in particular based on spatial, feedback or statistical analysis or information. Data from various data sources may be used for parametrizing the decision rule.

By way of example a decision rule based on spatial analysis or information may define that a pixel need to have, in addition to high enough intensity level, a specific CD location to be of interest. A decision rule based on feedback analysis or information, i.e. a feedback signal decision rule, can be for example based on an infinite impulse response (IIR) filter (including feedback part) based directional non-linear filter, which detects elongated intensity ridges or valleys of an original intensity image. A decision rule based on statistical analysis or information may take into account statistical measures, and utilize for example mean and standard deviation of the original or preprocessed input image data. Such a statistical rule can be used for separating 2D intensity and frequency contents of a "normal" product image from an "abnormal" behavior. The normal behavior (exhibited by normal quality product having normal, average, or standard quality, in particular quality complying with a given standard or norm) may be defined by statistical measures obtained based on one or more relatively large product area, having, in particular, dimensions $X_{global} \cdot y_{global}$. Subsequently, statistical measures obtained based on local measures may then be compared to the normal quality product statistical measures to define if the local pixel unit is of interest or not. Local measures, in particular current local frequency contents, may e.g. be obtained by a mean of CD and MD pixel-to-pixel difference results inside a defined local pixel neighborhood (having, in particular a dimension of $x_{local} \cdot y_{local}$ pixels, wherein, preferably $x_{local} << x_{global}$, $x_{global} \approx X$, $x_{global} \leq X$, $y_{local} << y_{global}$, $y_{global} \approx Y$, and/or $y_{global} \leq Y$,), which is not necessarily same as the defined local pixel unit (can be considered as preprocessing filtering method).

Figure 1B:
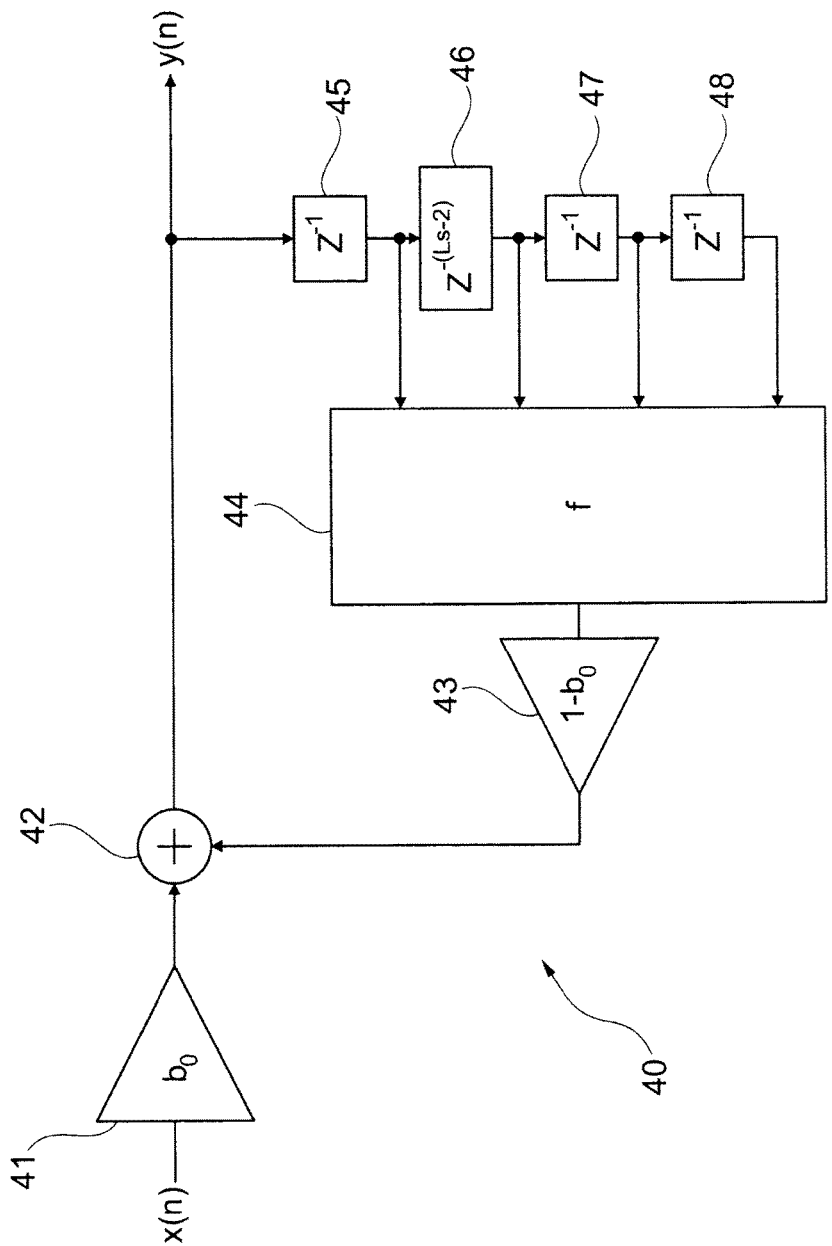
FIG. 1b shows an exemplary implementation of a decision rule based on feedback analysis or information.

FIG. 1b shows an exemplary implementation of a decision rule based on feedback analysis or information based on nonlinear IIR, wherein $$y(n)=b_0 x(n)+(1-b_0)f\{y(n-1), y(n-L_s+1), y(n-L_s), y(n-L_s-1)\},$$

where $b_0$ is the filter coefficient, x(n) is the input video signal, 44 is minimum or maximum function and $L_s$ is the length of a line. Thus, the new output y(n) is calculated as a weighted sum 42 of the old output, which is processed by a nonlinear feedback function 44, and the new input x(n). For instance, minimum function is used for dark defect detection and in proportion maximum function for light defect detection if low values correspond dark values in the intensity range. A two dimensional local environment is established by video signal delay elements Z 45-48. The filter coefficient $b_0$ controls the sensitivity of the detection. A longer defect, in machine direction, is needed for the lower defect signal levels, and, at the same time, a smaller filter coefficient value is needed.

If, based on an applicable decision rule, it is decided that the local pixel unit is of interest, it follows that the local pixel unit belongs to a region of interest, or is, at least, a candidate for being merged with one or more regions of interest, or for defining a new region of interest. As in the overwhelming majority of cases, however, a plurality of regions of interest will be present in the digital image, the region of interest to which the local pixel unit belongs has to be determined in a next step.

If a number n>0 of regions of interest $R_k$ with $k \in \{1; \ldots; n\}$ have already been identified during processing carried out so far, it is checked in a next step whether the local pixel unit may be deemed to belong to one of these regions of interest $R_k$ with $k \in \{1; \ldots; n\}$, or at least to a subset of regions of interest $R_k$ with $k \in A \subseteq \{1; \ldots; n\}$. The number n is a counter whose value is a natural number and represents a current number of regions of interest that have so far been identified. As more and more local pixel units or pixels are processed, this number may and generally will grow, as will become apparent from the description further down. At any instant, each region of interest represents a—or corresponds to a—subset of pixels $P_j$ with $j \in S \subset \{1; \ldots; P\}$ of the plurality of pixels of the digital image. As the processing of pixels continues, regions of interest and their corresponding subsets may change; in particular grow whenever a local pixel unit is deemed to belong to them.

To allow for simplifying and/or speeding up of the process of checking to which region of interest the local pixel unit may be deemed to belong, a concept of active regions may be introduced, wherein the active regions form a subset of the regions of interest $R_k$ with $k \in A_{active} \subseteq \{1; \ldots; n\}$, and wherein the check whether the local pixel unit may be deemed to belong to one of regions of interest that have been identified is limited to the active regions. The subset is repeatedly updated, wherein regions of interest may finalized, i.e. removed from the subset of active regions.

The check whether the local pixel unit belongs to a candidate region of interest $R_{kc}$ with $kc \in \{1; \ldots; n\}$ is done on the basis of an impact area Ake of said candidate region of interest $R_{kc}$. Similarly to a region of interest Rk, an impact area Ak represents a or corresponds to a subset of pixels $P_i$ with $i \in I_k \subset \{1; \ldots; P\}$ of the plurality of pixels of the digital image, which are generally located in and/or cover a neighborhood of the region of interest $R_k$ to which the impact area $A_k$ belongs. Practically speaking, adequately chosen impact areas may be used to allow for merging of local pixel units which are in a neighborhood of, or not further than a given maximum distance, in particular pixel distance, away from their respective candidate region of interest $R_{kc}$. Under an alternative approach, they will allow for merging of local pixel units which are located within defined 2D shapes of the impact areas, possibly under the further condition that their local features correspond to particular impact area features of the respective candidate region of interest $R_{kc}$.

An impact area $A_{k1}$ for a region of interest $R_{k1}$ may preferably be generated by building a distance map from every other region of interest $R_{k2}$ with k2!=k1, preferably by an infinite impulse response based filter, preferably with nonlinear environment processing.

Alternatively or in addition, a 2D shape and size of an impact area $A_{k1}$ for region of interest $R_{k1}$ may preferably be generated by building a directional distance map from every other region of interest $R_{k2}$ with k2!=k1, preferably by an infinite impulse response based filter, preferably with nonlinear environment processing. The source signal for the distance filter can be original intensity image, processed image or a feature value of the candidate region of interest $R_{kc}$, which causes the impact area shape (angle and distance from the respective candidate region of interest $R_{kc}$) to be dependent on the original image intensity, processed image intensity or features of the respective candidate region of interest $R_{kc}$.

Each impact area $A_k$ may thus also be considered to represent a or correspond to a subset of pixels $P_p$ with $p \in A_k \subset \{1; \ldots; P\}$ of the plurality of pixels comprised by the digital image.

If the concept of active regions is used, the check whether the local pixel unit may be deemed to belong to a region of interest is done for active regions only.

If the local pixel unit is located within the impact area $A_{kc}$ of the candidate region of interest $R_{kc}$, it may be merged with said candidate region of interest $R_{kc}$, resulting in a growth of said candidate region of interest $R_{kc}$ and of the subset of pixels said candidate region of interest $R_{kc}$ corresponds to or represents. Whether the local pixel unit and the candidate region of interest $R_{kc}$, are actually merged may be made dependent on an additional merging condition, which may, in particular, depend on properties or features, in particular current properties or features, of the candidate region of interest $R_{kc}$, in particular a shape, size, direction, local spatial frequency contents, intensity, in particular maximum, minimum, mean and/or average intensity, etc. of the said candidate region of interest $R_{kc}$. By way of example, a merging condition may specify that the local pixel unit shall or shall not be merged with elongated regions of interest, or shall or shall not be merged with at least approximately circular regions of interest.

If the local pixel unit is located within the impact area $A_{kc}$ of the candidate region of interest $R_{kc}$, and merged with said candidate region of interest $R_{kc}$, the impact area needs, at least in general, to be updated.

Preferably, it may also be checked whether the local pixel unit is located within impact area $A_{ko}$ of other regions of interest $R_{ko}$ with $ko \in \{1; \ldots; n\} \backslash \{kc\}$; and, if this is the case, such other regions of interest Rko may be updated.

Updating, in the above context, may in particular include updating of the impact area 2D shape filter and/or at least some, preferably all the feature values connected to the candidate region of interest $R_{kc}$ and/or the corresponding impact area $A_{kc}$, and/or other regions of interest $R_{ko}$ and/or respective impact areas $A_{ko}$.

If the local pixel unit is not located within an impact area $A_k$ of any of the regions of interest $R_k$ with $k \in \{1; \ldots; n\}$, or is not to be merged with any of the regions of interest $R_k$ with $k \in \{1; \ldots; n\}$ because additional merging conditions are not fulfilled, a new region $R_{n+1}$ of interest will preferably be initiated, and a new impact area $A_{n+1}$ will preferably be initialized for said new region $R_{n+1}$ of interest. Subsequently, the number n of regions of interest $R_k$ with $k \in \{1; \ldots; n\}$ that have already been identified during processing carried out so far is incremented by one according to n–>n+1.

If, based on the applicable decision rule, it is decided that the local pixel unit is not of interest, no merging with any of the regions of interest $R_k$ with $k \in \{1; \ldots; n\}$ needs to be done. Nevertheless, it is preferably checked in a next step whether the local pixel is located within an impact area $A_k$ of one the regions of interest $R_k$ with $k \in \{1; \ldots; n\}$ that have already been identified, or at least within an impact area $A_k$ of a subset of such regions of interest $R_k$ with $k \in A \subseteq \{1; \ldots; n\}$, and, if this is the case, the respective impact area $A_k$ may be updated.

Updating of a region of interest or an impact area may, in particular, imply that the subset of pixels the region of interest or impact area may be considered to represent or correspond to changes. As a consequence, properties or features, of the respective region or area, in particular a shape, size, direction, local spatial frequency contents, intensity, in particular maximum, minimum, mean and/or average intensity, area (size in number of pixels), size/extent in moving direction and/or cross direction, account within a defined measurement area, an angle (based on weight point tracking), a weight point, an intensity based weight point, a bounding box (in moving direction and/or cross direction), an average intensity, in particular within a measurement area of the region of interest, a maximum or minimum intensity, a roundness, information derived from an intensity histogram, local spatial frequency contents in various/different directions, etc. may also change.

In a preferred embodiment of the method in accordance with the present invention, a plurality of numerical values or other quantities representative of one or more features or properties may be determined for one or more regions of interest $R_k$ with $k \in \{1; \ldots; n\}$ and/or the corresponding impact areas $A_k$. Said numerical values or other quantities, may, in particular, be related to area (size in number of pixels), size/extent in moving direction and/or cross direction, account within a defined measurement area, an angle (based on weight point tracking), a weight point, an intensity based weight point, a bounding box (in moving direction and/or cross direction), an average intensity of the region of interest, an average intensity within a measurement area of the region of interest, a maximum or minimum intensity of the region of interest, a roundness, information derived from an intensity histogram, local spatial frequency contents in various/different directions, etc. The numerical values or other quantities may be stored, displayed and/or used for further analysis of the region of interest. In particular, morphometric methods, preferably real-time morphometric methods, may advantageously be applied in determining the numerical values or other quantities.

Further, a feature vector may be defined and determined for one or more of the regions of interest $R_k$ with $k \in \{1; \ldots; n\}$, and/or the corresponding impact areas $A_k$. A feature vector $v_k$ for a region of interest $R_k$ and/or the corresponding impact area $A_k$ contains one or preferably a plurality of numerical values or other quantities representative of one or more region or area features or properties as describe above. Components or entries from the feature vector may advantageously be used in a formulation of additional merging conditions. Background information related to feature vectors may be found under the related Wikipedia entry, e.g. https://en.wikipedia.org/w/index.php?title=Feature_vector&oldid=710384893 Whenever a local pixel unit is merged with a candidate region of interest $R_{kc}$, a feature vector $v_{kc}$ for said candidate region of interest $R_{kc}$ and/or the corresponding impact area $A_{kc}$ is preferably also updated subsequently.

The numerical values or other quantities representative of one or more region features or properties as describe above and/or the feature vectors $v_k$ are preferably used for classification and/or reporting of regions of interest $R_k$, and/or for further evaluation and/or control of the method in accordance with the present invention, preferably by way of post-processing.

Figure 2A:
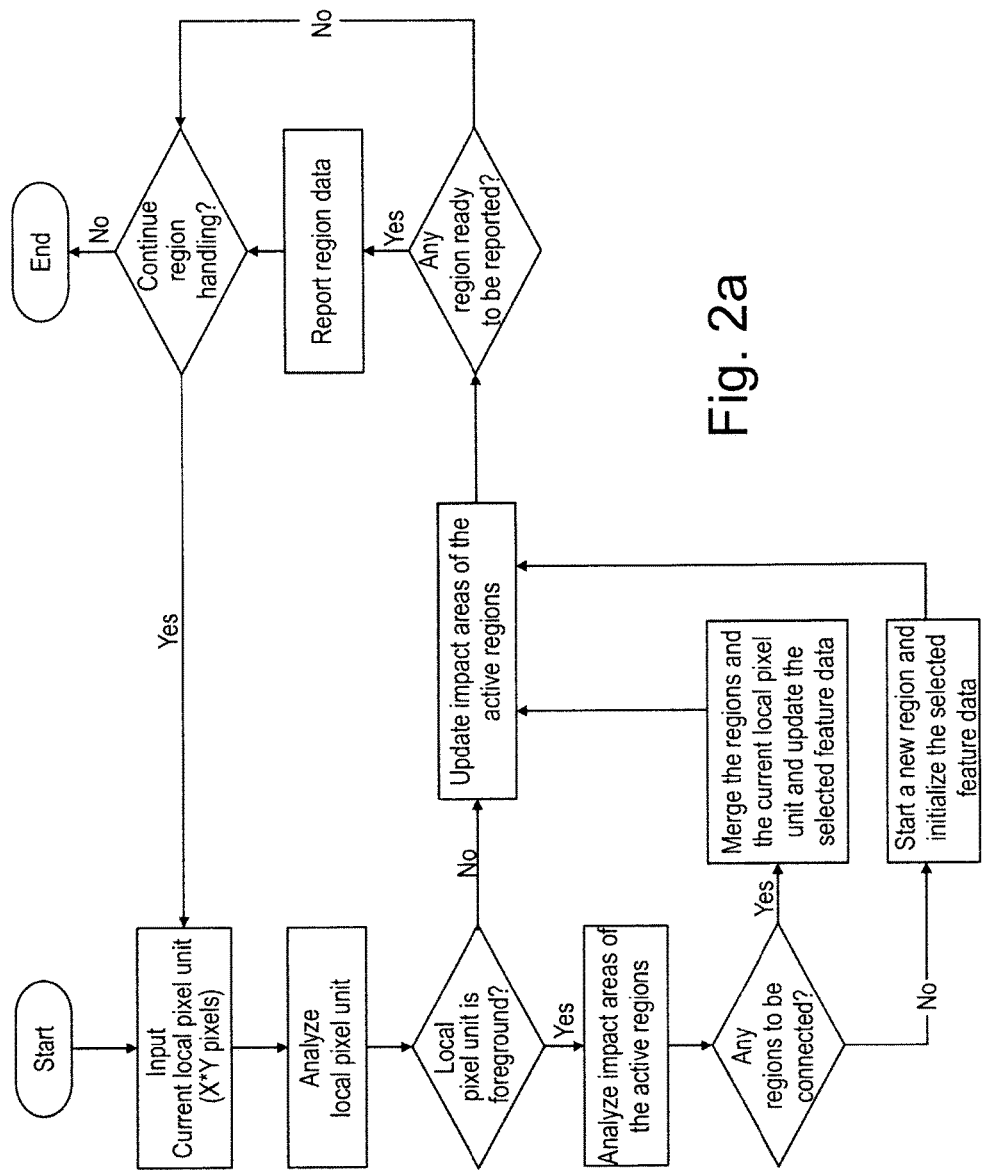
FIG. 2a shows a flow diagram of an exemplary implementation of the method in accordance with the invention.
Figure 2B:
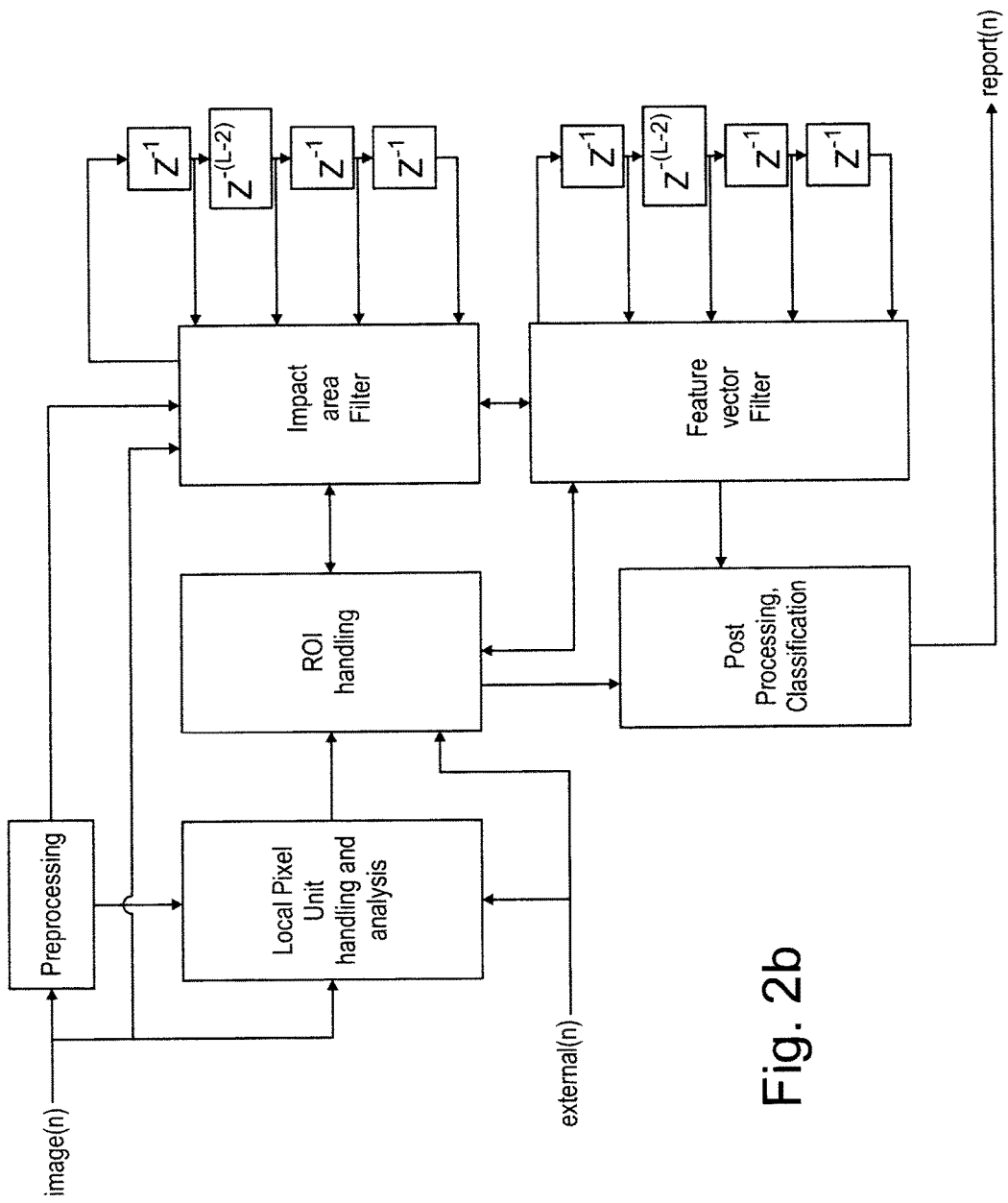
FIG. 2b shows an exemplary representation of the method in accordance with the present invention as a single pass filter.

For further illustration, FIG. 2a shows a flow diagram of an exemplary implementation of the method in accordance with the invention, in which it is assumed that a local pixel unit is of interest said local pixel unit is identified as a foreground region, e.g. based on intensity.

In a preferred embodiment of the method in a accordance with the present invention, the image as acquired is subjected to additional image processing, in particular through pre-processing and/or post-processing prior to and/or after digitization. In particular, adaptive flat line correction, a variant of flat field correction, may be applied to scans provided by the line scan camera, or to a composite image comprising several individual line scans. Alternatively or additionally, up- or downscaling with respect to bit-depth and/or spatial resolution may by applied as already indicated further above.

The method in accordance with the invention as described above allows for real-time application of morphometric methods to the regions of interest (ROIs) being identified. ROI segmentation processing allows for determining of the interesting regions of the imaged product. The next step is to analyze the regions and generate valuable information about the product quality. Morphometric refers to the methods measuring size and shape. These methods can be used to measure and generate geometric features and then it is possible to classify the interesting regions based on the features. Feature means a numerical value that is computable from binary image values and coordinates of the pixels in a region. When several features are extracted simultaneously a feature vector can be generated. With modern, field programmable gate array (FGPA) technology based hardware, which will be described in more detail below, and suitable algorithms, the morphometric parameters can be calculated in real-time from the streaming image data. An important parameter is Area, which is the total number of pixels of a region and can be used for region size classification. Area is also used for generating further geometric features. Another important geometric parameter is Perimeter of a region, which is the length of region's contour. Perimeter can also be used to generate several other geometric properties. For example Roundness can be derived by Roundness (Region) =$4\pi \cdot$(Area(Region))/ (Perimeter$^2$(Region)).

Figure 3:
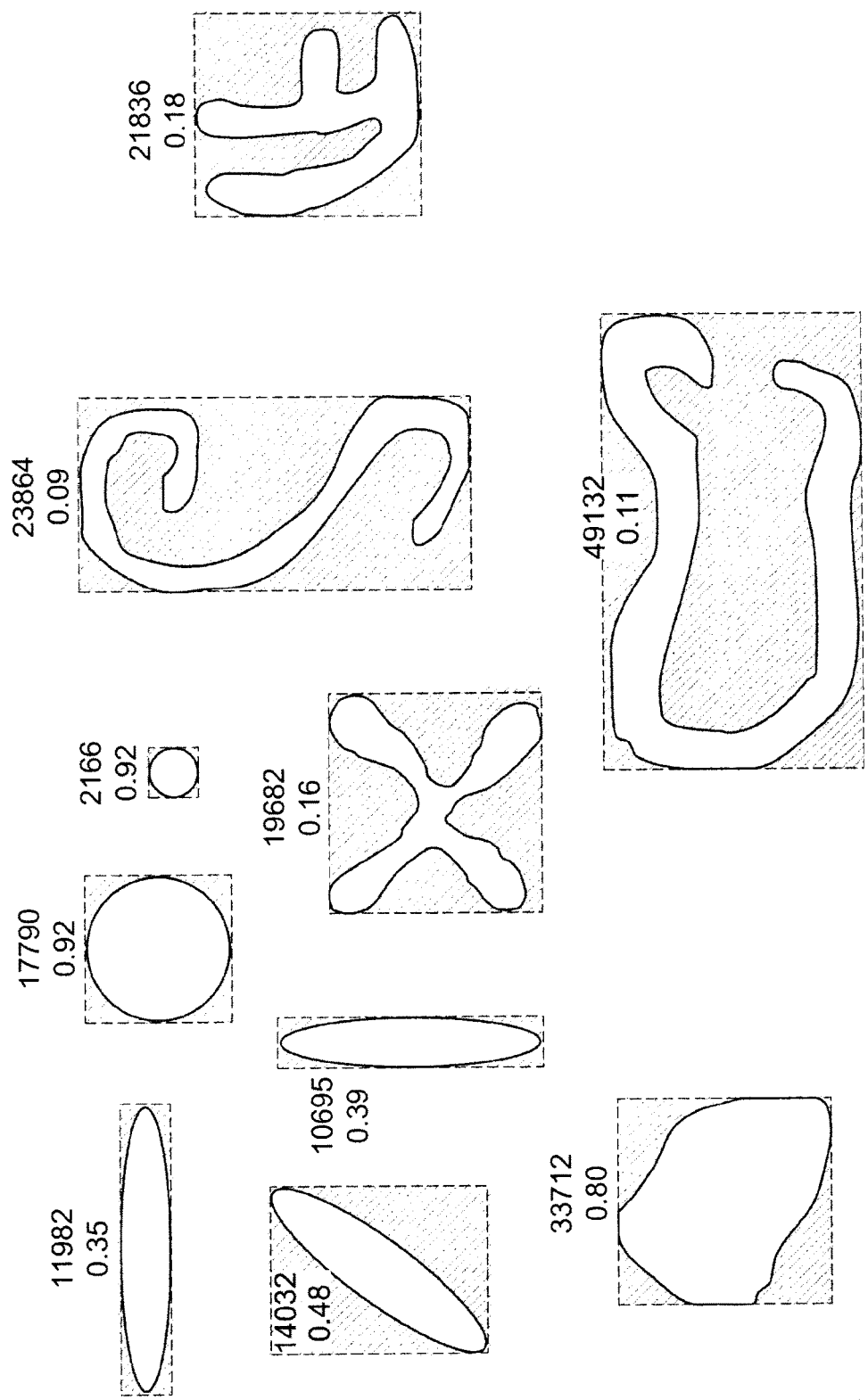
FIG. 3 shows exemplary regions of interest of various shapes.

Roundness and other ratio based calculated features are invariant to translation, rotation and scaling and thus they are reliable features to be used for region classification. Bounding box and Centroid are also valuable morphometric features and they can be derived from the region pixel coordinates. Exemplary shapes of regions of interest with measured Areas and calculated Roundness features are presented in FIG. 3. When comparing these shapes in FIG. 3 one can clearly see that for example Roundness feature separates well the circle type region (value 0.92) from the "flower" type region (value 0.16) while the area feature values are almost the same (17790 and 19682).

An FPGA is a programmable logic chip. A typical FPGA includes a large number of very simple logic elements which can each be configured to perform relatively simple logic functions. These logic elements can then be connected together to create more complex functionality. The complexity of the resulting logic is limited only by the number of logic elements and available interconnect routing resources. Historically, FPGAs were especially popular for prototyping designs based on the relatively short time required to make design changes, and reprogram the devices. Once the design was fully tested, it was typically implemented in an Application specific integrated circuit (ASIC). This allowed a manufacturer to save on ASIC development costs, and still exploit the benefits of high volume ASIC cost savings. Developments in FPGA technology allow today's devices to include millions of logic elements, support high internal clock frequencies, large internal memories, dedicated digital signal processing (DSP) blocks, and have competitive price levels. Today's FPGA technology is cost and performance competitive with ASIC technology in low to medium volume production applications. Unlike an ASIC device where the functionality is fixed, an FPGA device can be reprogrammed by downloading a user-defined configuration file. There are a wide variety of FPGA devices in the market, offering a multitude of dedicated features. One of the main advantages of FPGA devices is flexibility. General purpose processors are limited to fixed hardware features like for example the number of multipliers, amount of memory, amount of data paths and data widths. In an FPGA based design, application specific features can be configured and resource usage can be optimized as required.

Figure 4:
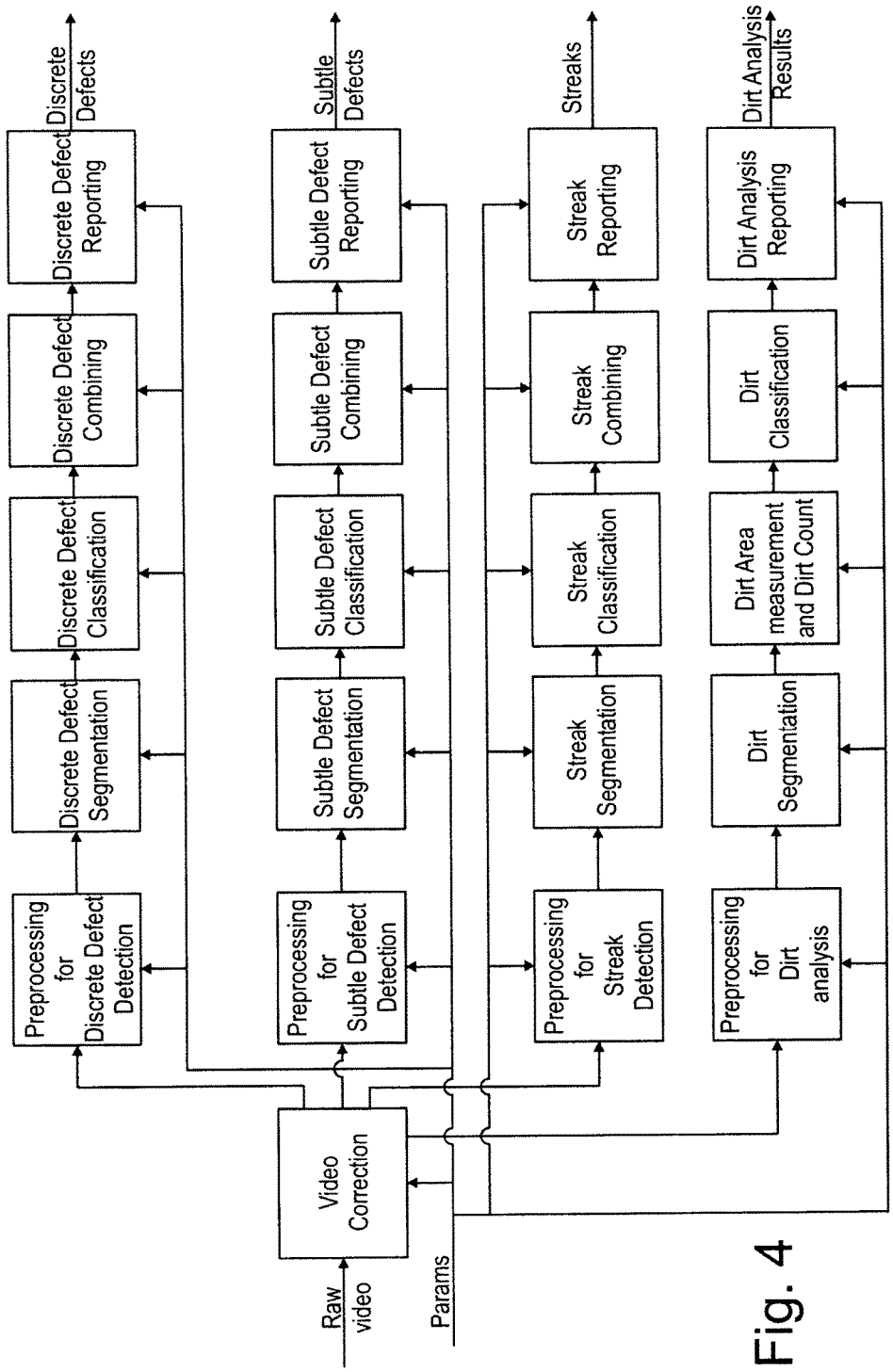
FIG. 4 shows an example of the parallel architecture of product imaging algorithms.

As described e.g. in Mittal, S., Gupta, S., and Dasgupta, S., "FPGA: An Efficient And Promising Platform For Real-Time Image Processing Applications", Proceedings of the National Conference on Research and Development in Hardware & Systems (CSI-RDHS), 2008, FPGAs are well suited for the real-time image processing applications typically needed in web imaging. Image processing algorithms require, or benefit from, support for spatial, temporal, computing and data parallelism, because usually a large number of operations should be performed utilizing multiple data sources for each pixel position. An example of the smart camera parallel architecture of the web imaging system is presented in FIG. 4. With an FPGA based system, it is also possible to design new algorithms later and add them to the system as parallel algorithms (for example new "soft imaging sensors").

The regions of interest in particular in pulp, paper, and paperboard product vary in size, shape and type. Thus, a single analysis method may not be capable of analyzing all of these regions optimally. Therefore, smart cameras with dedicated hardware and software may preferably be used instead of standard cameras. The multitude of defects, different requirements for analysis and thus different algorithms have set new requirements for the hardware. An example of the parallel architecture of product imaging algorithms is presented in FIG. 4. In web imaging systems, the first stage of the processing preferably includes a raw image capture with an imaging sensor. Then each of the different image analysis algorithms need dedicated image enhancement stages to maximize the signal-to-noise ratio before segmentation, i.e., the separation of the target object and background. The next stage of the processing is feature extraction based on the image data of the segmented ROIs. Calculated features are then used for region classification, which is the base for the intelligent image data filtering—only results of the regions having desired characteristics are reported. In typical systems, post processing methods are then used to combine some region analysis results before reporting. The last stage is the region data reporting, which may include also the region image generated using specific visualization requirements. Displaying and reporting of analysis results may, in particular, include defect maps that indicate precise areas where threshold limits have been exceeded, dedicated dirt summary tables that provide total defect area and number of defects in size groups, reporting according to ISO and TAPPI classification standards, online/offline defect maps, OPC interfaces with mill wide systems, and/or trending and profiling.

Figure 5:
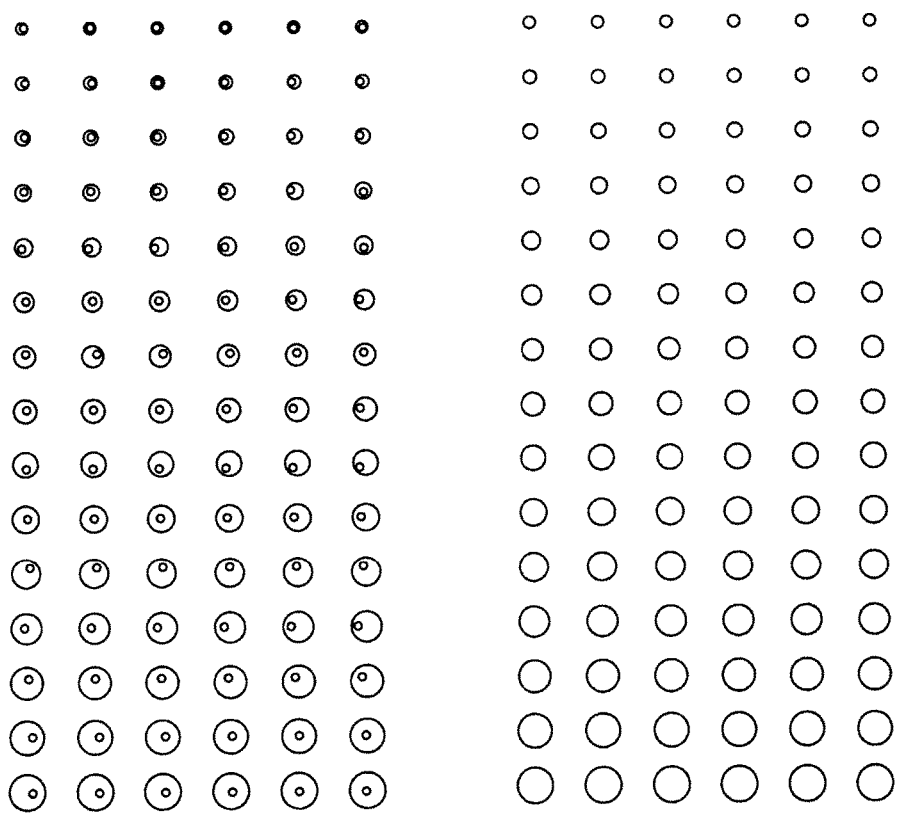
FIG. 5 shows a test pattern that was used for testing of the method in accordance with the invention
Figure 6:
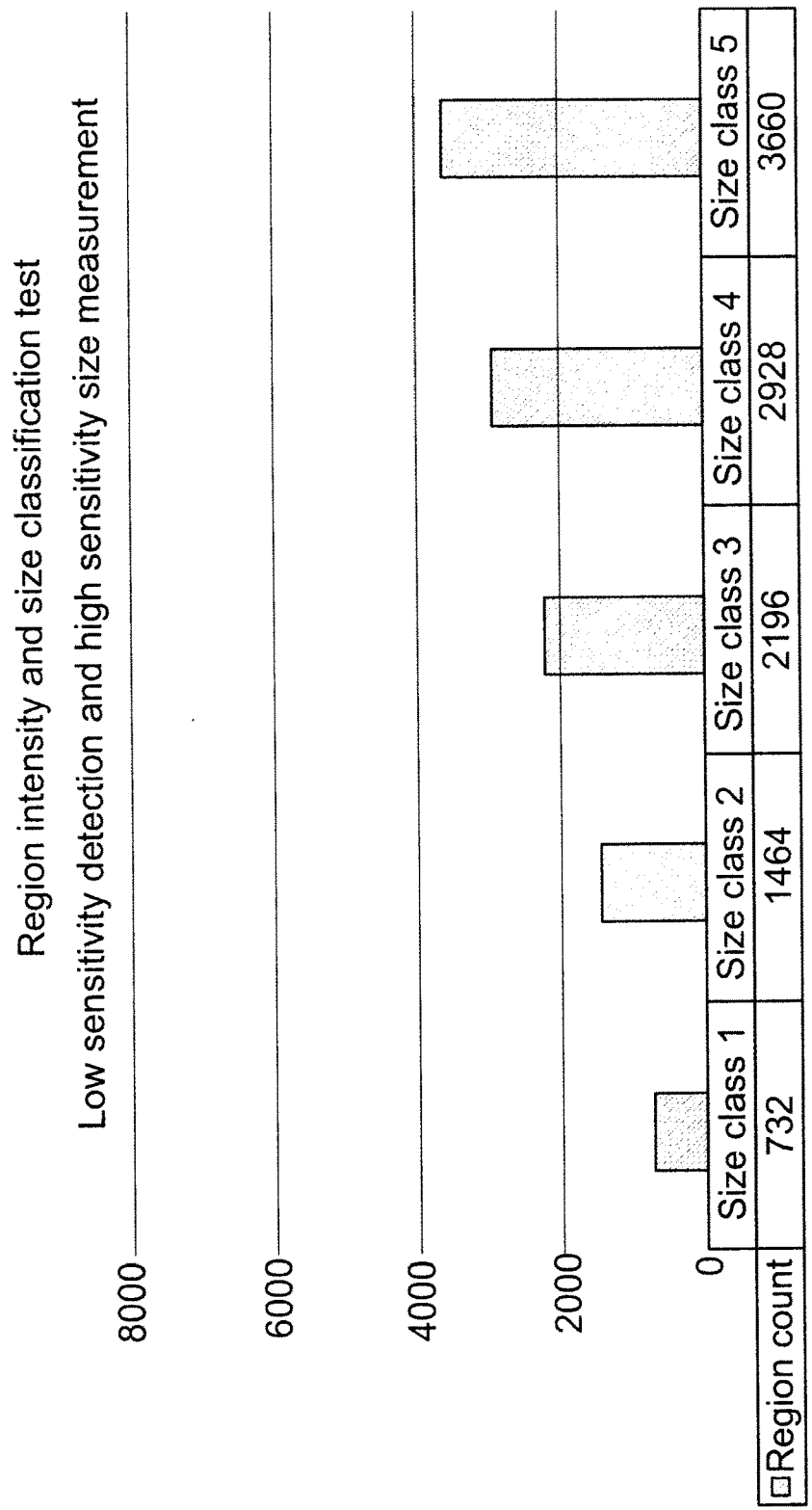
FIG. 6 shows results of the combined intensity and size classification test.
Figure 6:
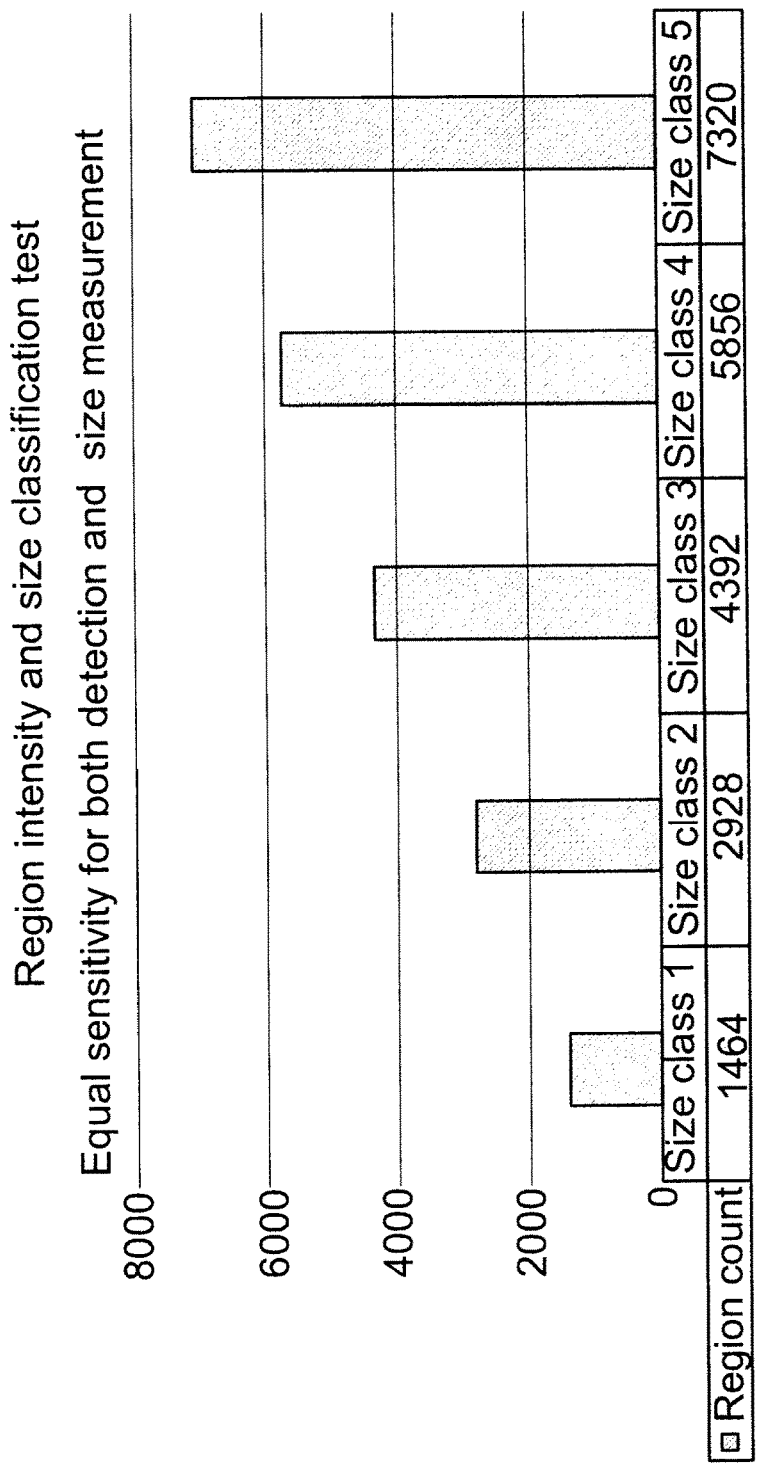

To test the capabilities of the method in accordance with the invention as described above, a test combining both intensity and size classification was carried to assess the performance of the system in a task where first a threshold value is set to find dots, and thereafter the size of the dot can be determined with another, potentially more sensitive threshold. A combination of intensity and size classification performance was carried out by utilizing a test pattern as shown in FIG. 5 consisting of 90 gray dots and 90 dots with gray and dark portions, 5 different size dots, which have areas of about 3.1 mm$^2$, 2.0 mm$^2$, 1.1 mm$^2$, 0.5 mm$^2$ and 0.2 mm$^2$, and starting from the largest size having count distribution of 6.7%, 13.3%, 20.0%, 26.7% and 33.3%. The test pattern was imaged by line scan imaging, using a rotating test drum for simulating a web speed of 115 m/min. Exposure time was 30 μs, and the test duration was 19.2 s. The test was done in two parts using two different detection threshold levels. By using a low sensitivity detection level, 10980 dot regions with dark dots inside the dot region were detected, their sizes were measured based on another, high sensitivity segmentation level, and the detected dots were classified based on the measured sizes. The results are shown in the upper chart in FIG. 6, which shows results of the combined intensity and size classification test. In this case, only the gray dots which had a dark region present in the left half of the test pattern as shown in FIG. 5 were detected for the region count due to the lower sensitivity detection level. By using a higher sensitivity detection level, all the 21960 gray/dark spots were detected as may be seen from the lower chart in FIG. 6. In this case, both the gray dots and the gray dots without (as shown in the right half of the test pattern of FIG. 5) and with a dark region (as shown in the left half of the test pattern of FIG. 5) were detected and measured for the region count. The count, size and intensity classification results correspond to the dark dot distribution in the test pattern, i.e., the system was capable of detecting dots with desired intensity high or low corresponding to the upper and lower chart in FIG. 6, to measure the size of the dots according to a sensitive segmentation level, and to classify the detected dots according to their sizes.

Unless stated otherwise, it shall be assumed throughout this entire document that a statement a≈b implies that $|a-b|/(|a|+|b|)<1$, preferably $|a-b|/(|a|+|b|)<10^{-1}$, and most preferably $|a-b|/(|a|+|b|)<10^{-2}$, wherein a and b may represent arbitrary variables as described and/or defined anywhere in this document, or as otherwise known to a person skilled in the art. Further, a statement that a is at least approximately equal or at least approximately identical to b implies that a≈b, preferably a=b. Further, unless stated otherwise, it shall assumed throughout this entire document that a statement a>>b implies that a>3b, preferably a>10b, most preferably a>100b; and statement a<<b implies that 3a<b, preferably 10a<b, most preferably 100a<b.

Preferred embodiments of the present invention, in particular as described above, may be realized as detailed in the items listed below, advantageously in combination with one or more of the features as detailed above:

1. A method for detection of distinctive features, in particular defects and/or formation irregularities, in a web being transported in a moving direction during a web manufacturing process, the method comprising the steps of
   a) acquiring an image of the web, said image being representable as a digital image comprising a plurality of pixels $P_i$ with $i \in \{1; \ldots; p\}$,
   b) identifying a plurality of regions of interest $R_k$ with $k \in \{1; \ldots; n\}$ each corresponding to a distinctive feature by processing the plurality of pixels $P_i$ by:
   c) selecting a local pixel unit comprising a subset $P_j$ with $j \in S \subset \{1; \ldots; p\}$ of the plurality of pixels, said subset
      i) being representative of a subregion of the digital image, and
      ii) different from previously selected local pixel units,
   d) deciding whether the local pixel unit is of interest or not,
      i) if the local pixel unit is of interest,
         1. identifying whether the local pixel unit is located within an impact area $A_k$ of a previously identified region of interest $R_k$ with $k \in A \subseteq \{1; \ldots; n\}$,
         2. if the local pixel unit is not located within any impact area $A_k$ of any previously identified region of interest $R_k$ with $k \in A \subseteq \{1; \ldots; n\}$, or no regions of interest have previously been identified,
            a) identifying the local pixel unit as a new region $R_{n+1}$ of interest;
            b) initializing an impact area $A_{n+1}$ for said new region $R_{n+1}$ of interest
         c) incrementing a counter n representative of the number of previously identified regions of interest;
         3. if the local pixel unit is located within an impact area $A_{k0}$ of a previously identified region of interest $R_{k0}$, a) merging, depending on a merging condition, the local pixel unit with said previously identified region of interest $R_{k0}$,
b) if the merging condition is fulfilled, updating the impact area $A_{k0}$ of said region of interest $R_{k0}$;
e) repeating steps b) through d) until at least essentially all pixels of the image have been processed.
2) The method according to item 1, wherein in step d)
    i) if the local pixel unit is not of interest,
        1. identifying whether the local pixel unit is located within an impact area $A_k$ of a previously identified region of interest $R_k$ with $k \in \{1; \ldots; n\}$,
        2. if the local pixel unit is located within an impact area $A_{k0}$ of a previously identified region of interest $R_{k0}$, updating said impact area $A_{k0}$.
3) The method according to one of the previous items, wherein the local pixel unit comprises a plurality of pixels, in particular a subset of pixels acquired by a line scan camera.
4) The method according to one of the previous items, wherein the step of deciding whether the local pixel unit is of interest or not comprises determining whether an intensity, in particular an average, median, minimum, or maximum pixel intensity, of the local pixel unit is above or below a threshold value.
5) The method according to one of the previous items, wherein the step of deciding whether the local pixel unit is of interest or not is based on spatial, feedback or statistical information, in particular obtained from previously processed pixels.
6) The method according to one of the previous items, wherein the step of deciding whether the local pixel unit is of interest or not is based on additional data from at least additional source, in particular on connected region handling information.
7) The method according to one of the previous items, wherein an impact area A is generated for each region of interest $R_k$ with $k \in \{1; \ldots; n\}$.
8) The method according to one of the previous items, wherein an impact area is characterized by a subset $P_l$ with $l \in I \subset \{1; \ldots; N\}$ of the plurality of pixels of the digital image, preferably representing a coherent, two-dimensional shape.
9) The method according to one of the previous items, wherein a feature vector is determined for each region of interest $R_k$ with $k \in \{1; \ldots; n\}$.
10) The method according to one of the previous items, wherein an impact area $A_{k1}$ for region of interest $R_{k1}$ is generated by building a distance map from every other region of interest $R_{k2}$ with $k2 \neq k1$, preferably by an infinite impulse response based filter with nonlinear environment processing.
11) The method according to one of the previous items, further comprising the steps of
    a) setting the number n of previously identified regions of interest to zero in or prior to step b) of item 1,
    b) when at least essentially all pixels of the image have been processed, reporting the current value of n as a number of distinctive features found.
12) The method according to one of the previous items, further comprising the steps of
    a) after step f) of item 1, determining morphometric features of at least one region of interest $R_k$ with $k \in \{1; \ldots; n\}$.
13) An optical web inspection system comprising
    a) an image acquisition unit (12) for acquiring an image of a web (11) being transported in a moving direction during a web manufacturing process,
    b) a digitization unit, preferably comprised by the image acquisition unit,
    c) a processing unit (17) configured to execute the method according to one of items 1 through 11, wherein a local pixel unit is provided by the digitization unit,
    d) a display unit (16) for displaying results, in particular a number n of regions of interest $R_k$ with $k \in \{1; \ldots; n\}$ identified.
14) The optical web inspection system according to the previous item, characterized in that the processing unit comprises a field-programmable gate array.

The invention claimed is:
1. A computer implemented method for detection of distinctive features, in particular defects and/or formation irregularities, in a web being transported in a moving direction during a web manufacturing process, the method comprising the steps of:
    a) acquiring an image of the web, said image being representable as a digital image including a plurality of pixels $P_i$ with $i \in \{1; \ldots; P\}$,
    b) identifying a plurality of regions of interest $R_k$ with $k \in \{1; \ldots; n\}$, each corresponding to a distinctive feature, by processing the plurality of pixels $P_i$ by:
    c) selecting a local pixel unit including a subset $P_j$ with $j \in S \subset \{1; \ldots; P\}$ of the plurality of pixels, said subset being representsative of a subregion of the digital image and different from a previously selected local pixel unit,
    d) deciding, based on a decision rule, whether the local pixel unit is of interest or not, wherein if the local pixel unit is of interest:
        1) identifying whether the local pixel unit is located within an impact area $A_k$ of a previously identified region of interest $R_k$, in particular any one of the previously identified regions of interest $R_k$, with $k \in A \subseteq \{1; \ldots; n\}$, wherein the impact area $A_k$ represents or corresponds to a subset of pixels $P_i$ with $i \in I_k \subset \{1; \ldots; P\}$ of the plurality of pixels of the digital image, which are at least generally located in and/or cover a neighborhood of the region of interest $R_k$ to which the impact area $A_k$ belongs,
        2) if the local pixel unit is not located within any impact area Ak of any previously identified region of interest $R_k$ with $k \in A \subseteq \{1; \ldots; n\}$, or no regions of interest have previously been identified,
            identifying the local pixel unit as a new region $R_{n+1}$ of interest;
            initializing an impact area $A_{n+1}$ for said new region $R_{n+1}$ of interest
            incrementing a counter n representative of the number of previously identified regions of interest;
        3) if the local pixel unit is located within an impact area $A_{k0}$ of a previously identified region of interest $R_{k0}$,
            merging, depending on a merging condition, the local pixel unit with said previously identified region of interest $R_{k0}$,
            if the merging condition is fulfilled, updating the impact area $A_{k0}$ of said region of interest $R_{k0}$,
            wherein the merging condition depends on properties or features of the previously identified region of interest $R_{k0}$, said properties or features including at least one of a shape, size, or direction of said region of interest $R_{k0}$, e) repeating steps b) through d) until at least all pixels of the image have been processed.

2. The method according to claim 1, wherein in step d), the local pixel unit is merged with the previously identified region of interest $R_{k0}$ if the merging condition is fulfilled, and is not merged with the previously identified region of interest $R_{k0}$ if the merging condition is not fulfilled.

3. The method according to claim 1, wherein the merging condition requires that the previously identified region of interest $R_{k0}$ is at least elongated.

4. The method according to claim 1, wherein the merging condition requires that the previously identified region of interest $R_{k0}$ is at least approximately circular.

5. The method according to claim 1, wherein if the local pixel unit is not of interest;
   1) identifying whether the local pixel unit is located within an impact area $A_k$ of a previously identified region of interest $R_k$ with $k \in \{1; \ldots; n\}$,
   2) if the local pixel unit is located within an impact area $A_{k0}$ of a previously identified region of interest $R_{k0}$, updating said impact area $A_{k0}$.

6. The method according to claim 1, wherein the local pixel unit includes a subset of pixels acquired by a line scan camera.

7. The method according to claim 1, wherein the step of deciding whether the local pixel unit is of interest or not includes determining whether an intensity, in particular an average, median, minimum, or maximum pixel intensity, of the local pixel unit is above or below a threshold value.

8. The method according to claim 1, wherein the step of deciding whether the local pixel unit is of interest or not is based on spatial, feedback or statistical information, in particular obtained from previously processed pixels.

9. The method according to claim 1, wherein the step of deciding whether the local pixel unit is of interest or not is based on additional data from at least one additional source.

10. The method according to claim 1, wherein an impact area $A_k$ is generated for each region of interest $R_k$ with $k \in \{1; \ldots; n\}$.

11. The method according to claim 1, wherein an impact area is characterized by a subset $P_l$ with $l \in I \subset \{1; \ldots; N\}$ of the plurality of pixels of the digital image, preferably representing a coherent, two-dimensional shape.

12. The method according to claim 1, wherein a feature vector $v_k$ is determined for each region of interest $R_k$ and/or the corresponding impact area $A_{k0}$, with $k \in \{1; \ldots; n\}$.

13. The method according to claim 1, wherein a feature vector $v_{k0}$ of the previously identified region of interest $R_{k0}$ and/or the corresponding impact area $A_{k0}$ is taken into consideration when evaluating whether or not the merging condition is fulfilled.

14. The method according to claim 1, wherein an impact area $A_{k1}$ for region of interest $R_{k1}$ is generated by building a distance map from every other region of interest $R_{k2}$ with k2!=k1, preferably by an infinite impulse response based filter with nonlinear environment processing.

15. The method according to claim 1, further including the steps of:
   setting the number n of previously identified regions of interest to zero in or prior to step b),
   when at least all pixels of the image have been processed, reporting the current value of n as a number of distinctive features found.

16. The method according to claim 1, further including the steps of:
   after step e), determining morphometric features of at least one region of interest $R_k$ with $k \in \{1; \ldots; n\}$.

17. The method according to claim 1, wherein the merging condition depends on a shape or direction of the previously identified region of interest $R_{k0}$.

18. An optical web inspection system comprising:
   an image acquisition unit for acquiring an image of a web being transported in a moving direction during a web manufacturing process,
   a digitization unit,
   a processing unit configured to execute a method for detection of distinctive features in the web, the method includes:
   a) acquiring an image of the web, said image being representable as a digital image including a plurality of pixels $P_i$ with $i \in \{1; \ldots; P\}$,
   b) identifying a plurality of regions of interest $R_k$ with $k \in \{1; \ldots; n\}$, each corresponding to a distinctive feature, by processing the plurality of pixels $P_i$ by:
   c) selecting a local pixel unit including a subset $P_j$ with $j \in S \subset \{1; \ldots; P\}$ of the plurality of pixels, said subset being representative of a subregion of the digital image and different from a previously selected local pixel unit,
   d) deciding, based on a decision rule, whether the local pixel unit is of interest or not, wherein if the local pixel unit is of interest:
      1) identifying whether the local pixel unit is located within an impact area $A_k$ of a previously identified region of interest $R_k$, in particular any one of the previously identified regions of interest $R_k$, with $k \in A \subseteq \{1; \ldots; n\}$, wherein the impact area $A_k$ represents or corresponds to a subset of pixels $P_i$ with $i \in I_k \subset \{1; \ldots; P\}$ of the plurality of pixels of the digital image, which are at least generally located in and/or cover a neighborhood of the region of interest $R_k$ to which the impact area $A_k$ belongs,
      2) if the local pixel unit is not located within any impact area Ak of any previously identified region of interest $R_k$ with $k \in A \subseteq \{1; \ldots; n\}$, or no regions of interest have previously been identified,
         identifying the local pixel unit as a new region $R_{n+1}$ of interest;
         initializing an impact area $A_{n+1}$ for said new region $R_{n+1}$ of interest
         incrementing a counter n representative of the number of previously identified regions of interest;
      3) if the local pixel unit is located within an impact area $A_{k0}$ of a previously identified region of interest $R_{k0}$,
         merging, depending on a merging condition, the local pixel unit with said previously identified region of interest $R_{k0}$,
         if the merging condition is fulfilled, updating the impact area $A_{k0}$ of said region of interest $R_{k0}$,
         wherein the merging condition depends on properties or features of the previously identified region of interest $R_{k0}$, said properties or features including at least one of a shape, size, or direction of said region of interest $R_{k0}$,
   e) repeating steps b) through d) until at least all pixels of the image have been processed
   the digitization unit providing a local pixel unit, and
   a display unit for displaying results, in particular a number n of regions of interest $R_k$ with $k \in \{1; \ldots; n\}$ identified.

19. The optical web inspection system according to claim 18, wherein the processing unit includes a field-programmable gate array.

* * * * *